(12) United States Patent
Glauser et al.

(10) Patent No.: US 6,894,246 B2
(45) Date of Patent: May 17, 2005

(54) VARIABLE ENVIRONMENT LASER WELD SYSTEM

(75) Inventors: Dominique Glauser, St-Sulpice (CH); Jose Garcia, Lelocle (CH); Jean-Francois Fischer, Etoy (CH); Stephane Rohrer, Neuchatel (CH); Eric F. Davila Lozada, Humacao, PR (US); Yan Cardineau, Phoenix, AZ (US); Claude Brist, Ham Lake, MN (US); Chris J. Paidosh, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 252 days.

(21) Appl. No.: 10/202,814

(22) Filed: Jul. 25, 2002

(65) Prior Publication Data

US 2004/0016725 A1 Jan. 29, 2004

(51) Int. Cl.[7] .............................................. B23K 20/14
(52) U.S. Cl. ................................................ 219/121.63
(58) Field of Search ........................ 219/121.86, 121.84, 219/121.63, 121.64, 121.65, 121.66

(56) References Cited

U.S. PATENT DOCUMENTS

| 4,021,898 A | * | 5/1977 | Willis et al. ............... 29/25.35 |
| 4,041,956 A | | 8/1977 | Purdy et al. ............. 128/419 P |
| 4,162,390 A | | 7/1979 | Kelly |
| 4,845,331 A | * | 7/1989 | Yeo et al. ...................... 219/72 |
| 4,868,068 A | * | 9/1989 | Yamaguchi et al. ........ 428/596 |
| 5,344,432 A | | 9/1994 | Slettenmark et al. |
| 5,370,669 A | | 12/1994 | Daglow et al. |
| 5,535,752 A | | 7/1996 | Halperin et al. ............. 128/670 |
| 5,564,434 A | | 10/1996 | Halperin et al. ............. 128/748 |
| 5,640,764 A | | 6/1997 | Strojnik ....................... 29/856 |
| 5,843,140 A | | 12/1998 | Strojnik ....................... 607/36 |

FOREIGN PATENT DOCUMENTS

| EP | 0288585 | 2/1988 |
| JP | 06071434 | 3/1994 |
| JP | 2001353589 | 12/2001 |

* cited by examiner

Primary Examiner—Jonathan Johnson
(74) Attorney, Agent, or Firm—Girma Wolde-Michael

(57) ABSTRACT

A welding system with variable environment system is provided that allows devices to be welded in different gas environments. The preferred welding system uses a controllable gas delivery system that provides different gas mixtures to a welding chamber at different times. Thus, welding in different gas mixtures can be performed in a single welding chamber. This allows the devices to be welded both in environments that promote effective welding and in environments that have specific characteristics desirable for gases that remain in the completed device. Thus the system facilitates the formation of different types of devices in a single welding chamber, and in a single manufacturing line.

20 Claims, 2 Drawing Sheets

VARIABLE ENVIRONMENT LASER WELD SYSTEM

BACKGROUND OF THE INVENTION

1. Field of the Invention

This invention generally relates to welding systems, and more specifically relates to welding systems for implantable devices.

2. Description of Related Art

In modern manufacturing systems it is often desirable to have the ability to manufacture different types of devices in the same manufacturing line. By reducing the need for additional manufacturing equipment and lines, the overall efficiency of the manufacturing system is improved. Improving the efficiency of the system provides the ability to produce devices at lower costs, an important factor in today's competitive world economy.

One type of manufacturing system commonly used in a wide variety of applications are laser welding systems. Laser welding systems use lasers to provide automated welding on production devices. In an automated laser welding system, devices are brought into a welding chamber and held by a tool. A laser is then used to perform welding on the device. The whole process is typically controlled by a computer to make the welding as automated as possible.

When attempting to manufacture different devices with different operational requirements, the welding environment can be a significant issue. For example, it is generally desirable to weld devices in an inert, weld-friendly environment. This improves the quality of the weld and the finished device. Unfortunately, the gases that make up the weld-friendly environment may not provide the operational requirements for some types of devices. These devices require a different type of gas be inside the device before it is welded shut.

An example of this problem is found in the manufacturing of implantable cardiac devices. Implantable cardiac devices include a wide range of different types of medical devices. For example, implantable pulse generators (IPGs) are a type of cardiac device that is used to steady the rhythm of a beating heart. This type of device, often referred to as a Bradycardia device or a pacemaker, do not require operational high voltages. Another type of implantable cardiac device are implantable cardiac defibulators (ICDs). This type of device, often referred to as a Tachycardia device, can be used to provide a defibulator shock to the heart when a heart problem is sensed. These ICD devices have significantly greater voltage requirements than the IPG devices.

To provide the voltage needed by the ICD, these devices are typically formed with a high dielectric gas, such as a nitrogen mixture, inside the device. Thus, they must be welded shut or sealed in a nitrogen gas mixture. In contrast, IPG devices do not require the high voltage and thus are typically welded shut with an inert welding gas, such as an argon mixture, inside the device. These differences in gas requirements have led in the past to these devices being manufactured in different processing lines. This lowers the efficiency of the system, and results in overall higher costs to consumers.

Thus, what is needed is an improved welding system that provides for different welding environments and thus allows different types of devices to be formed on a manufacturing line.

BRIEF SUMMARY OF THE INVENTION

The present invention provides a welding system with a variable environment system that allows devices to be welded in different gas environments. The preferred welding system uses a controllable gas delivery system that provides different gas mixtures to a welding chamber at different times. Thus, welding in different gas mixtures can be performed in a single welding chamber. This allows the devices to be welded both in environments that promote effective welding and in environments that have specific characteristics desirable for gases that remain in the completed device. Thus the welding system facilitates the formation of different types of devices in a single welding chamber, and in a single manufacturing line.

The preferred embodiment is particularly applicable to a welding system for forming implantable cardiac devices. In these embodiments, the variable environment system allows some welding to be performed in inert gas environment that is conducive to effective welding while allowing other welding to be performed in gas environments chosen for their electrical properties. This allows both implantable pulse generators (IPGs) and implantable cardiac defibulators to be formed in the same manufacturing line, reducing manufacturing cost and improving overall efficiency.

The foregoing and other objects, features and advantages of the invention will be apparent from the following more particular description of a preferred embodiment of the invention, as illustrated in the accompanying drawings.

BRIEF DESCRIPTION OF DRAWINGS

The preferred exemplary embodiment of the present invention will hereinafter be described in conjunction with the appended drawings, where like designations denote like elements, and.

DETAILED DESCRIPTION OF THE INVENTION

The embodiments of the present invention provide a welding system with a variable environment system that allows devices to be welded in different gas environments. The preferred welding system uses a controllable gas delivery system that provides different gas mixtures to a welding chamber at different times. Thus, welding in different gas mixtures can be performed in a single welding chamber. This allows the devices to be welded both in environments that promote effective welding and in environments that have specific characteristics desirable for gases that remain in the completed device. Thus the system facilitates the formation of different types of devices in a single welding chamber, and in a single manufacturing line.

Figure 1:
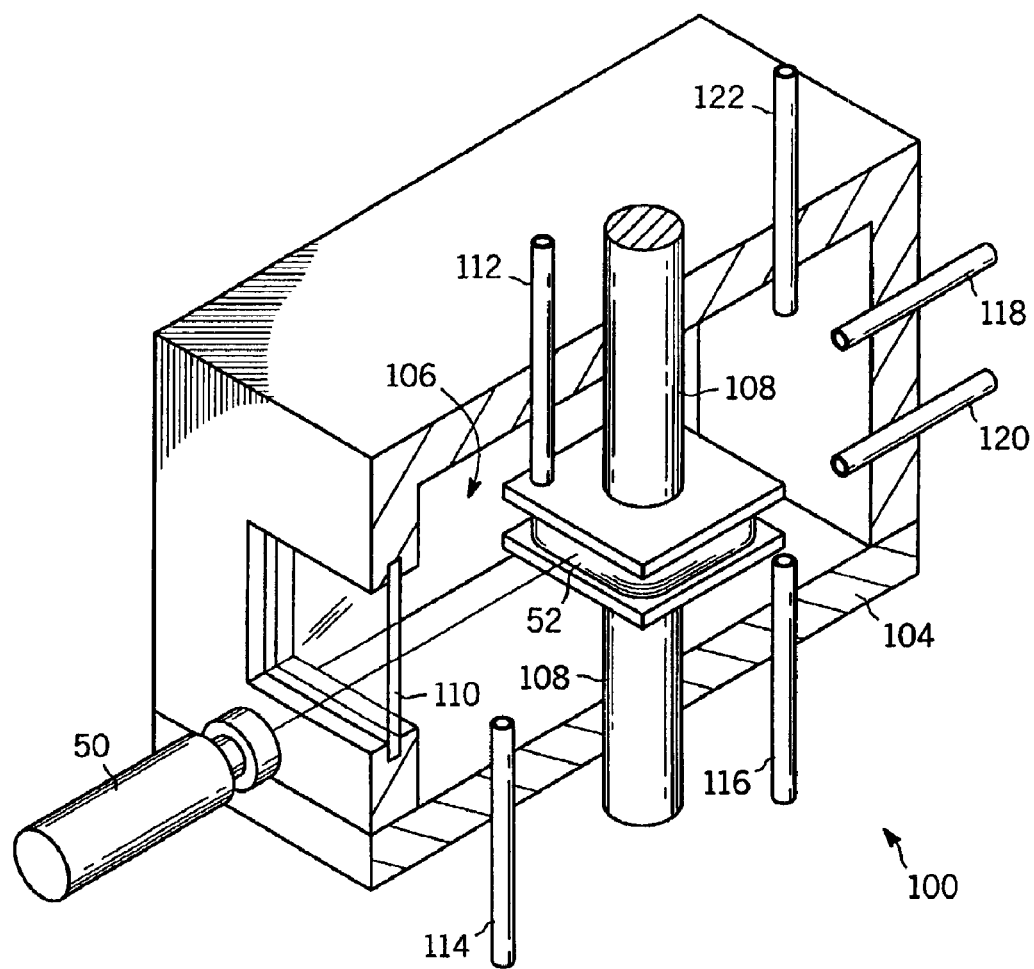
FIG. 1 is a cross-sectional isometric view of a welding chamber.

Turning now to FIG. 1, an exemplary welding chamber 100 is illustrated. The welding chamber 100 provides an environment in which a device 52 may be welded by a laser 50. The welding chamber 100 includes an upper case portion 102 and a lower case portion 104 with a seal between them. When the upper case portion 102 and lower case portion 104 are brought together, they define a sealed welding area 106, and when separated allow device 52 to be brought in and out of the welding chamber 100. The welding chamber 100 includes a holding tool 108 for catching and holding the device 52 when it is to be welded by laser 50. The welding chamber 100 also includes a window 110 that allows the laser 50 to weld the device 52 from outside the welding chamber 100 while provide a gas seal for the welding area 106. The welding chamber 100 also includes a vacuum line 112 that allows gases from the welding process to be efficiently removed. The welding chamber 100 also includes debris removal lines 118 and 120, and a direct welding gas intake line 122. Finally, the welding chamber 100 includes gas lines 114 and 116 that are used to provide the needed different gas mixtures during the welding process. Specifically, gas lines 114 and 116 are used to provide inert weld friendly gases during some welding processes and gases selected for specific electrical properties during other welding processes.

The upper case portion 102 and lower case portion 104 can be controllable separated and closed using any suitable mechanical movement system. For example, pneumatic cylinders can be used to raise the upper case portion 102 when a device 52 is to be inserted into the welding chamber 100. When the device 52 is held by the holding tool 108, the pneumatic cylinders can then pull the upper case portion 102 down to the lower case portion 104, providing the gas sealed welding area.

Likewise, the holding tool 108 can be opened and closed using any suitable mechanical movement system. Again, pneumatic cylinders can be used to raise and lower the upper and lower portions of the holding tool 108 to provide a secure hold on the device 52 during welding. Typically, these cylinders would also allow the device 52 to be lowered and raised during welding, allowing different portions of the device 52 to be welded. Also, the holding tool 108 would typically also provide the ability to rotate device 52 to allow for welding on all horizontal sides of device 52.

During welding operation, the device 52 is delivered to the welding chamber 100 using any suitable motion system, such as the various computer controlled conveyor systems that are commonly used in automated fabrication systems. With the upper case portion 102 separated from the lower portion 104, the device 52 is delivered to the holding tool 108. The upper and lower portions of the holding tool 108 clamp together to secure the device 52. The upper case portion 102 and lower case portion 104 are then brought together to provide a gas sealed welding area 106.

Next, the air is removed from the welding area 106 using the vacuum line 112. When the welding area 106 is brought to a sufficient vacuum, the welding area 106 is then filled with an appropriate gas through gas lines 114 and/or 116. In some cases, the gas would be selected to provide an inert welding environment, such as an argon gas mixture. In other cases, the gas would be one that is selected for particular electrical properties, such as a nitrogen gas mixture. The device 52 can then be welded using laser 50. During welding, some welding gas can be provided directly onto the welding area using the welding gas supply line 122. Also during welding, the debris removal lines 118 and 120 can be used to remove soot that could otherwise contaminate the welding process. When welding is completed, the remaining gases can be removed using the vacuum line 112.

Thus, the welding chamber 100 provides the ability to weld devices in a variety of gas mixtures, and thus provides the ability to weld different types of devices in one welding chamber and thus in one manufacturing line.

The preferred embodiment is particularly applicable to a welding system for forming implantable cardiac devices. In these embodiments, the variable environment system allows some welding to be performed in inert gas environment that is conducive to effective welding while allowing other welding to be performed in gas environments chosen for their electrical properties. This allows both implantable pulse generators (IPGs) and implantable cardiac defibulators (ICDs) to be formed in the same manufacturing line, reducing manufacturing cost and improving overall efficiency.

Implantable cardiac devices are generally made with two main parts that need to be welded together to complete the device. When the two parts are welded together, it is desirable to weld the devices in an inert, weld-friendly environment. For example, when the two parts are welded together it can be done in a mixture of argon and helium, with argon providing an inert welding environment and helium providing the ability to perform leak detection. When the two parts are welded together in an argon mixture, the inside of the completed implantable cardiac device is left filled with the argon gas mixture. While this is acceptable in some devices, it is unacceptable in others.

In particular, implantable pulse generators (IPGs) (also referred to as Bradycardia devices and pacemakers) and other low voltage devices do not generally require any specific electrical properties for the inside gas. Thus in making these devices, a gas delivery system can provide the inert weld friendly argon gas mixture in the welding chamber 100 during welding, with this gas mixture sealed inside the completed device.

In contrast, implantable cardiac defibulators (ICDs) (also referred to as Tachycardia devices) and other high voltage devices often require an interior gas that increases the dielectric voltage and increases the trace density internally. This allows for a reduction in interior volume, and thus can result in reduced device size. For example, a mixture of nitrogen and helium can be provided inside the devices. The nitrogen provides the increased dielectric voltage, and the helium again provides leak detection.

While nitrogen provides an increased dielectric, it is generally provides a poor welding environment. Specifically, the nitrogen can result in embrittlement of the metals such as titanium in the ICD if present during significant welding.

ICDs, like IPGs are commonly made with two main parts, commonly called shield halves, which are put together and welded in the welding chamber 100. In order to facilitate the inclusion of a high dielectric gas into the completed device, a backfill hole is also provided in at least one of the parts. When welding ICDs within the welding chamber, the vacuum line 112 again removes all the air, and then an argon gas or other weld friendly gas mixture is provided through gas lines 114 and/or 116. The two parts are then welded together with the laser 50. The vacuum line 112 is then used to remove the argon gas mixture. The welding chamber is then filled with a nitrogen gas or other high dielectric gas mixture. The exact dielectric requirements for the gas mixture would depend upon the amount of voltage used by the device and the geometry of the device. The backfill hole in the device allows the inside of the ICD to be filled with the nitrogen mixture. The backfill hole is then closed with a short weld directed at the hole. This weld seals the ICD, with a portion of the high dielectric gas mixture inside. Although this weld is done in a less weld-friendly environment, its short duration minimizes any negative effects that would otherwise occur.

Furthermore, a cover gas can also be provided to improve welding conditions during the backfill weld. In this case a cover gas, such as argon, is preferably connected to a nozzle that sprays the argon gas directly over the portion of the device that is being welded. This allows argon cover gas to be sprayed over the device when it is being welded in a nitrogen gas mixture. This reduces the negative effects of welding in the nitrogen gas mixture while also minimizing the amount of argon that enters the device through the backfill hole. Thus, the weld operation gets some of the benefit of welding in an argon mixture while the device is still filled with primarily a nitrogen gas mixture.

The welding chamber 100 can thus be used to weld both IPG and ICD devices, with the majority of the welding done in a weld friendly gas mixture and ICD devices being filled with a high dielectric gas before final sealing.

The welding chamber 100 would be used as part of a larger manufacturing system used to automate the manufacturing off both IPG and ICD devices. That system would typically include a conveyor line used to deliver the devices to the welding chamber, and a handling system that automatically performs the loading to the holding tool and the alignment of shield halves for the IPG/ICD devices. In the manufacture of IPG and ICD devices, the holding tool also provides the required clamping pressure to close any gaps and to restrain both halves prior to the laser welding. To accomplish this, the holding tool grips the device using both a bottom actuator that plunges the part up from the conveyer and a top actuator that pushes down to hold the device.

The laser welding is performed using any suitable laser, such as a ND-Yag laser with pulse energies up to 2.2(J), and frequencies of up to 45 Hz, available from Lumonics, Inc. as model JK702. The conveyor line, handling and environment controls would preferably be controlled by a computer system that administers the motion, welding, environment and ancillary systems. This would typically include the ability to weld complex, non-linear seams on the device.

Figure 2:
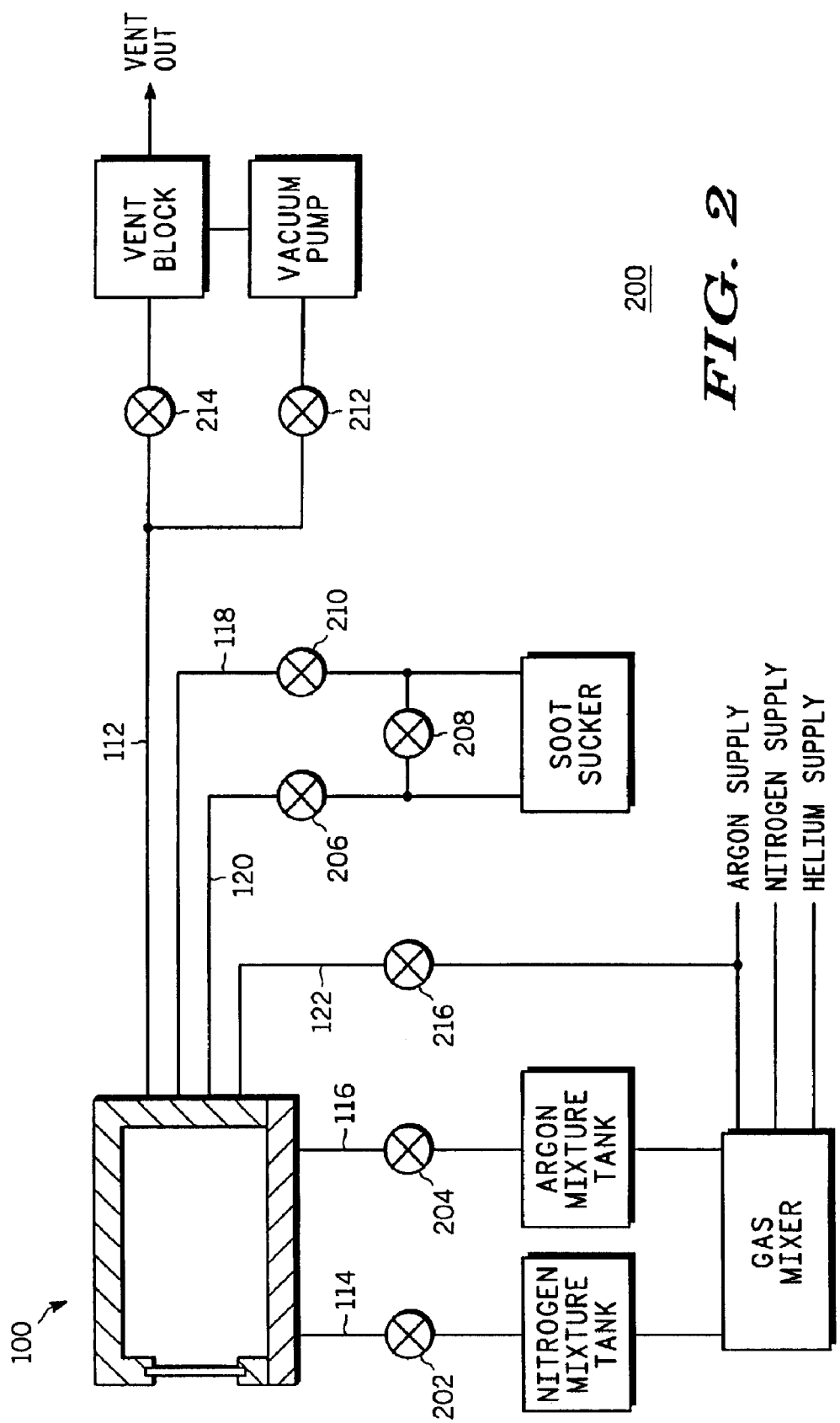
FIG. 2 is schematic diagram of the welding chamber with a gas delivery and vacuum system.

Turning now to FIG. 2, a more detailed view is illustrated of a preferred gas delivery and vacuum system 200 for use with the welding chamber 100. The gas delivery and vacuum system 200 includes an argon gas mixture tank, a nitrogen mixture tank, a gas mixer that receives an argon supply, nitrogen supply and a helium supply. The system 200 also includes a direct argon supply line 122 to supply an argon cover gas during some welding. The system 200 also includes a soot sucker for filtering particles generated during the welding. The soot sucker includes a blower that pulls gas and particles during welding through a filter and returns the gas free of particles to the welding chamber 100. The system 200 also includes a vacuum pump and vent block for removing gases from the welding chamber after welding. Finally, the system includes valves 202–216 that allow the various gases and vacuums to be selectively provided to the welding chamber 100.

The gas mixer receives an argon supply line, a nitrogen supply line and a helium supply line. The gas mixer mixes these gases to come up with the desired weld-friendly argon/helium gas mixture and the high dielectric nitrogen/helium mixture. For example, the gas mixer can mix 80% argon with 20% helium to form welding gas mixture, and 80% nitrogen with 20% helium to form a high dielectric gas mixture. The gas mixer provides these gas mixtures to the respective holding tanks, the argon mixture tank and the nitrogen mixture tank. The valves 202 and 204 allow the argon gas mixture and nitrogen gas mixture to be selectively provided to the welding chamber, thus providing for welding in both a weld friendly environment and a high dielectric environment.

The argon supply is also connected directly to the welding chamber through valve 216. This argon supply line is preferably connected to a nozzle that sprays the argon gas directly over the portion of the device that is being welded. This allows argon cover gas to be sprayed over the device when it is being welded in a nitrogen gas mixture, reducing the negative effects of welding in the nitrogen gas mixture while also minimizing the amount of argon that enters the device through the backfill hole.

The soot sucker is used to remove welding debris from the chamber during welding, and includes a blower and filter element. Thus, it is connected to a suction nozzle in the welding chamber that is proximate the welding area. During welding, the valves 206 and 210 open, while valve 208 closes. This allows the blower to pull out debris and gas from the welding chamber, filter the gas and send the filtered gas back to the welding chamber 100. When the welding is complete, the valves 206 and 210 close, while 208 opens, and the soot sucker re-circulates the gas while waiting for the next weld.

The vacuum pump is used to pull the welding chamber down to vacuum, removing air, welding and high dielectric gases as needed. The vent block provides outer vent from the welding chamber and from the vacuum pump to where gases can be safely released. The valve 212 controls when the vacuum pump is removing gases from the welding chamber and valve 214 controls when the welding chamber is vented to where gases can be released.

It should be noted that valves 202–216 can be any suitable type of gas control valve that can be selectively opened and closed, such as gas valves that are pneumatically operated. The operation of the valves would be preferably controlled by the computer system that automates the fabrication system. Likewise, lines 112–122 can be implemented any suitable gas line materials.

Thus, the preferred embodiments of the present invention provide welding system with a variable environment system that allows devices to be welded in different gas environments. The preferred welding system uses a controllable gas delivery system that provides different gas mixtures to a welding chamber at different times. Thus, welding in different gas mixtures can be performed in a single welding chamber. This allows the devices to be welded both in environments that promote effective welding and in environments that have specific characteristics desirable for gases that remain in the completed device. Thus the system facilitates the formation of different types of devices in a single welding chamber, and in a single manufacturing line. The preferred embodiment is particularly applicable to a welding system for forming implantable cardiac devices. In these embodiments, the variable environment system allows some welding to be performed in an inert gas environment that is conducive to effective welding while allowing other welding to be performed in gas environments chosen for their electrical properties. This allows both implantable pulse generators (IPGs) and implantable cardiac defibulators to be formed in the same manufacturing line, reducing manufacturing cost and improving overall efficiency.

While the invention has been particularly shown and described with reference to a preferred exemplary embodiment thereof, it will be understood by those skilled in the art that various changes in form and details may be made therein without departing from the spirit and scope of the invention.

What is claimed is:

1. A welding system, the welding system comprising:
   a) a welding chamber, the welding chamber providing an environment for welding a device; and
   b) a gas delivery system coupled with the welding chamber for delivering gas into the welding chamber;
   c) a first gas supply coupled with the gas delivery system and containing a welding gas; and d) a second gas supply coupled with the gas delivery system and containing a dielectric gas, wherein the gas delivery system further includes a control mechanism for selectively coupling the first gas supply to the welding chamber or the second gas supply to the welding chamber.

2. The welding system of claim 1 wherein the welding system further includes a vacuum system to remove gases from the welding chamber.

3. The welding system of claim 1 wherein the gas delivery system includes a welding gas delivery line coupled with the first gas supply and a dielectric gas delivery line coupled with the second gas supply.

4. The welding system of claim 3 wherein the first gas supply includes a welding gas mixture storage tank coupled to the welding gas delivery line and the second gas supply includes a dielectric gas mixture storage tank coupled to the dielectric gas delivery line, the welding gas mixture storage tank storing an inert welding gas mixture that includes the welding gas and the dielectric gas mixture storage tank storing a dielectric gas mixture that includes the dielectric gas.

5. The welding system of claim 4, wherein the control mechanism further comprises a welding gas mixture control valve and a dielectric gas mixture control valve, the welding gas mixture control valve coupled along the welding gas delivery line to control delivery of the welding gas mixture, the dielectric gas mixture control valve coupled along the dielectric gas delivery line to control delivery of the dielectric gas mixture.

6. The welding system of claim 1 wherein the welding gas comprises argon gas and wherein the dielectric gas comprises a nitrogen gas.

7. The welding system of claim 1 wherein the welding chamber includes a holding tool for holding the device during welding.

8. The welding system of claim 1 wherein the gas delivery system further includes a cover gas supply to provide cover gas to the welding chamber during welding.

9. A welding system for welding implantable cardiac defibrillators and implantable pulse generators, the welding system comprising:
   a) a welding chamber, the welding chamber selectively receiving the implantable cardiac defibrillators and the implantable pulse generators for welding; and
   b) a gas delivery system coupled with the welding chamber for delivering gas into the welding chamber;
   c) a first gas supply coupled with the gas delivery system and containing a welding gas for welding of the implantable cardiac defibrillators and the implantable pulse generators; and
   d) a second gas supply coupled with the gas delivery system and containing a dielectric gas for further welding of the implantable cardiac defibrillators, wherein the gas delivery system further includes a control mechanism for selectively coupling the first gas supply to the welding chamber or the second gas supply to the welding chamber.

10. The welding system of claim 9 wherein the welding system further includes a vacuum system to remove gases from the welding chamber.

11. The welding system of claim 9 wherein the first gas supply further includes a welding gas mixture storage tank coupled to the welding chamber through a welding gas delivery line and the second gas supply further includes a dielectric gas mixture storage tank coupled to the welding chamber through a dielectric gas delivery line, the welding gas mixture storage tank storing an inert welding gas mixture and the dielectric gas mixture storage tank storing a dielectric gas mixture.

12. The welding system of claim 11, wherein the control mechanism further includes a welding gas mixture control valve and a dielectric gas mixture control valve, the welding gas mixture control valve coupled along the welding gas delivery line to control delivery of the welding gas mixture, the dielectric gas mixture control valve coupled along the dielectric gas delivery line to control delivery of the dielectric gas mixture.

13. The welding system of claim 11 wherein the inert welding gas mixture comprises an argon gas mixture and wherein the dielectric gas mixture comprises a nitrogen gas mixture.

14. The welding system of claim 9 wherein the gas delivery system further includes a cover gas supply to provide cover gas to the welding chamber during welding.

15. The welding system of claim of claim 4, wherein the inert welding gas mixture includes argon and the dielectric gas mixture includes nitrogen.

16. The welding system of claim 15, wherein the welding gas mixture further includes helium and the dielectric gas mixture further includes helium.

17. The welding system of claim 4, further comprising:
   a gas mixer coupled with the welding gas mixture tank and the dielectric gas mixture tank;
   a third gas supply coupled with the gas mixer and containing the welding gas;
   a fourth gas supply coupled with the gas mixer and containing the dielectric gas;
   a fifth gas supply coupled with the gas mixer and containing a mixing gas, wherein the gas mixer selectively mixes the welding gas and the mixing gas to form the inert gas mixture and delvers the inert gas mixture to the welding gas mixture storage tank and mixes the mixing gas and the dielectric gas to form the dielectric gas mixture and delivers the dielectric gas mixture to the dielectric gas mixture storage tank.

18. The welding system of claim 17, wherein the mixing gas is a seal testing gas.

19. The welding system of claim 17, wherein the mixing gas is helium.

20. The welding system of claim 17, further comprising:
   a first gas inlet disposed within the welding chamber for delivering the welding gas; and
   a second gas inlet disposed within the welding chamber for delivering the dielectric gas.

* * * * *